United States Patent [19]

Schiff

[11] Patent Number: 4,473,067

[45] Date of Patent: Sep. 25, 1984

[54] INTRODUCER ASSEMBLY FOR INTRA-AORTIC BALLOONS AND THE LIKE INCORPORATING A SLIDING, BLOOD-TIGHT SEAL

[76] Inventor: Peter Schiff, Rte. 7, Cookeville, Tenn. 38501

[21] Appl. No.: 372,631

[22] Filed: Apr. 28, 1982

[51] Int. Cl.³ .................... A61B 19/00; A61M 25/00
[52] U.S. Cl. .................. 128/1 D; 604/158; 604/167
[58] Field of Search ............... 604/158–170; 128/1 D, 785

[56] References Cited

U.S. PATENT DOCUMENTS

| | | | |
|---|---|---|---|
| 3,902,501 | 9/1975 | Citron et al. | 128/785 |
| 4,014,333 | 3/1977 | McIntyre | 604/167 X |
| 4,096,860 | 6/1978 | McLaughlin | 604/167 X |
| 4,166,469 | 9/1979 | Littleford | 604/164 X |
| 4,233,982 | 11/1980 | Bauer et al. | 604/169 X |
| 4,306,562 | 12/1981 | Osborne | 604/164 |
| 4,327,709 | 5/1982 | Hanson et al. | 128/1 D |

FOREIGN PATENT DOCUMENTS 1064445 5/1954 France .............................. 604/158

*Primary Examiner*—Dalton L. Truluck

*Attorney, Agent, or Firm*—Louis Weinstein

[57] ABSTRACT

An assembly for introducing intra-aortic balloons and the like into a body artery and comprising a thin, splittable sheath positioned within the artery. An intra-aortic balloon and balloon catheter are inserted into the femoral artery through the introducer sheath. An adapter is slidably mounted upon the balloon catheter and is provided with cutters for splitting the thin introducer sheath, which is at least partially withdrawn from the body once the intra-aortic balloon is in place. The adapter is provided with a silicone seal which provides a sliding, blood-tight seal between the adapter and the balloon catheter. The adapter may be provided with a retainer for releasably supporting an annular elastic member to hold the percutaneous sheath tightly in place about the adapter body to provide a blood-tight seal therebetween. The resilient element may further include a self-contained suture or a groove for receiving a suture to further tighten the percutaneous sheath about the adapter, providing a blood-tight seal between sheath and adapter and between adapter and balloon catheter. The sheath may be scored to facilitate splitting and thereby eliminate the need for a cutter. The sheath may be provided with a "handle portion" or a pre-cut slit to initiate splitting of the sheath.

30 Claims, 19 Drawing Figures

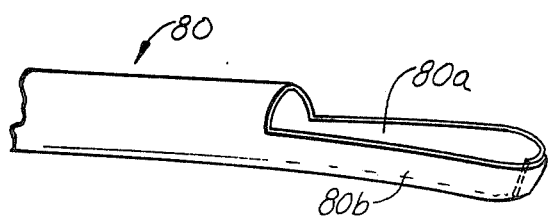
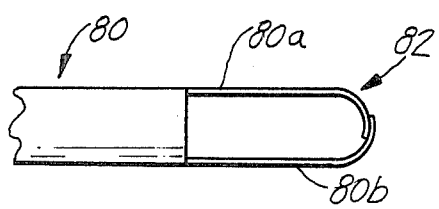
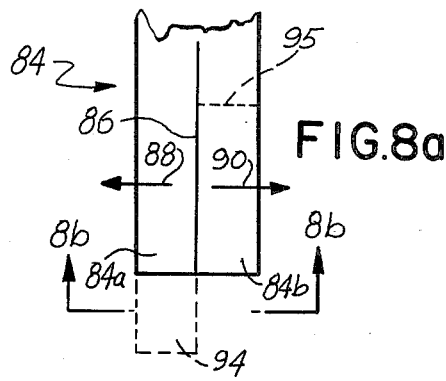
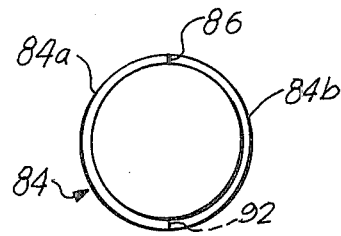
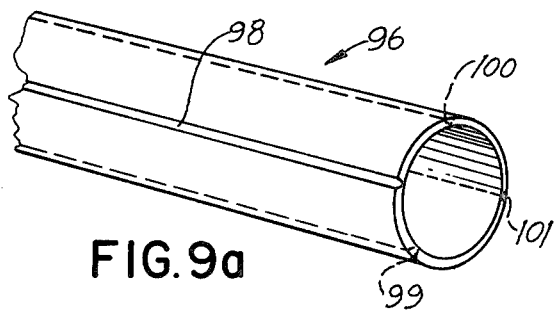
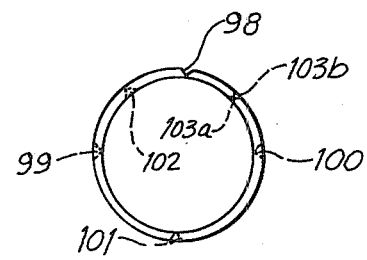
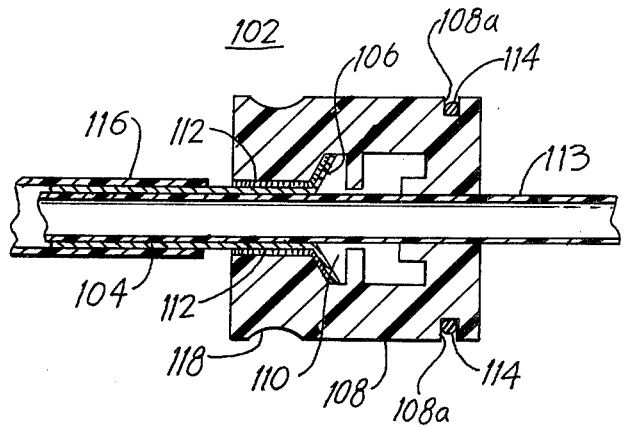
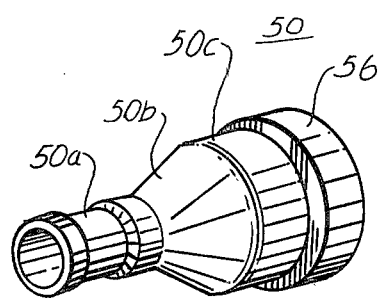

INTRODUCER ASSEMBLY FOR INTRA-AORTIC BALLOONS AND THE LIKE INCORPORATING A SLIDING, BLOOD-TIGHT SEAL

BACKGROUND OF THE INVENTION

In recent years, mechanical assist devices have been developed for assisting the heart, especially a weak or impaired heart, in the blood pumping function. One such mechanical assist device is the intra-aortic balloon. A technique for introducing the intra-aortic balloon into the body has been developed, which technique enables the intra-aortic balloon to be inserted percutaneously. In using the percutaneous technique, the intra-aortic balloon is twisted or wrapped to significantly reduce its outer diameter prior to insertion. The intra-aortic balloon is then inserted into a percutaneous sheath which extends at least partially into an artery such as, for example, the femoral artery.

The sheath presently employed for percutaneous insertion has a relatively short length.

Arterial disease often makes it difficult to pass the intra-aortic balloon through the vascular system. The difficulty is especially pronounced when attempting to move the intra-aortic balloon past the bifurcation in the abdomen that branches the abdominal aorta into the right and left illiac arteries and, in turn, into the two femoral arteries. It is therefore extremely desirable to have a long percutaneous introducer sheath that is positioned well into the large abdominal aorta or even the thoracic aorta by means of a guide wire with a J-type tip. The long percutaneous sheath of the introducer allows the intra-aortic balloon to be placed past such obstructions and totally avoids subjecting the intra-aortic balloon to the lacerating insults of a build-up of arterial plaque.

The introducer sheath does, however, present some disadvantages. For example, once the intra-aortic balloon is properly placed, through the use of the percutaneous method, the long introducer sheath increases the overall size (*i.e. outer diameter*) of the effective balloon catheter with which it has been inserted in the artery and thereby obstructs the flow of blood within that artery to the leg, causing clotting and circulatory complications. To solve this problem, the introducer sheath is withdrawn from the body along the balloon catheter requiring that the balloon catheter itself be quite long, further necessitating that the balloon catheter be provided with a larger lumen for the extra length, to permit fast balloon actuation. The percutaneous introducer has the disadvantage of not being able to pass beyond the intra-aortic balloon to the extension hose coupling due to the large outer diameter of said coupling.

Another sheath removal technique which has been employed to alleviate this problem is to provide a peel-apart introducer sheath which is comprised of a sheath which is designed to peel apart due to only moderate stretching. In use, the sheath is inserted to the proper location within the body and thereafter the balloon is inserted, whereupon the sheath is withdrawn and either entirely or partially peeled away from the catheter. The peel-apart introducer sheath is similar to those employed in cardiac procedures when placing the pacing wires, utilized for example with pacemakers and the like. The peel-apart sheath is formed of a grain-oriented plastic material to facilitate splitting in an orderly manner.

The long sheath, which is typically of the order of sixteen inches in length, after being removed entirely, leaves only the small diameter balloon catheter within the femoral artery. Due to the small balloon catheter diameter, relative to the inner diameter of the femoral artery, excellent circulation is assured. However, removal of the sheath from the femoral artery, which necessarily has a larger diameter than the balloon catheter, may cause a potential bleeding problem when the smaller balloon catheter is the only remaining member penetrating the opening originally formed in the femoral artery to introduce the percutaneous sheath, balloon and balloon catheter.

BRIEF DESCRIPTION OF THE INVENTION

The above disadvantage is overcome by only partially removing the sheath, in order to significantly reduce and even eliminate the potential bleeding problem. In addition, the portion of the introducer sheath remaining facilitates the removal of the intra-aortic balloon and also facilitates the insertion of a second intra-aortic balloon which may be introduced to replace the original intra-aortic balloon (for whatever purpose). A sufficient amount of sheath is left in the body so that at least a small portion thereof extends into the interior of the femoral artery. The portion of the sheath within the femoral artery further simplifies removal of the balloon through the sheath rather than pulling the balloon which presents an irregular surface to the artery. It is important, however, to seal the sheath around the balloon catheter without obstructing the balloon catheter lumen. This is difficult to accomplish, requiring the placement of a suture tightly about the sheath but without cutting off the passageway of the catheter.

In order to significantly simplify and facilitate the peeling-apart of an introducer sheath, the present invention is characterized by providing a balloon catheter adapter slidably mounted upon the balloon catheter and arranged to split a lengthy introducer sheath by movement of the sheath and catheter relative to one another, while providing a sliding blood-tight seal between the introducer sheath and the balloon catheter regardless of the position of the adapter along both the sheath and the catheter.

The sheath is preferably a thin gauge tubular member formed of teflon or other similar material, avoiding the need for a grain-oriented material.

Present-day peel-apart sheaths tend to peel apart prematurely due, for example, to obstructive conditions within the artery. The peel-apart sheaths are also expensive. To avoid both the expense and the premature peeling apart of the introducer sheath, a standard sheath of a suitable gauge may be substituted to achieve all of the advantages of a peel-apart sheath while eliminating the two last-mentioned disadvantages.

The adapter is provided with at least one integral cutting member, spaced inwardly from a tapered forward edge which stretches and enlarges the introducer sheath as it is about to engage the cutting edge. By moving either the adapter or introducer sheath or both, in opposing directions, the sheath is split as it is being removed from the femoral artery.

The introducer sheath may further be provided with a marker band or other appropriate indication indicating the appropriate length of the introducer sheath which should remain intact in order to have at least a portion thereof extending into the interior of the femoral artery.

The sliding blood-tight seal is accomplished by providing a resilient element bonded to the catheter adapter and slidably engaging the balloon catheter to assure that a good, blood-tight seal is provided even though the catheter adapter is moved relative to the balloon catheter.

In order to further advance the blood-tight seal between the introducer sheath and the catheter adapter, the adapter may be fitted with a retainer ring upon which is mounted a stretchable elastic collar which holds the introducer sheath tightly about the adapter to provide a blood-tight seal between the introducer sheath and the adapter. The retainer ring, with or without an elastic collar mounted thereon, protects the operator from engaging the blade.

The sheath employed with the adapter need not be of the peel-apart type, since the cutting member serves to easily sever the sheath. To facilitate the cutting operation, the end of the sheath engaging the cutting member may be provided with at least one pre-cut slit. The end of the sheath adjacent the slit may incorporate an integral extension for use as a gripping handle to facilitate movement of the sheath against the adapter to initiate splitting of the sheath. As another alternative, the sheath may be provided with a pair of integral extensions joined at their free ends to form a gripping loop to facilitate movement of the sheath against the adapter to initiate splitting of the sheath.

As another alternative, the sheath may be provided with an axially aligned score (or scores) to facilitate splitting of the sheath.

OBJECTS OF THE INVENTION AND BRIEF DESCRIPTION OF THE FIGURES

It is, therefore, one object of the present invention to provide a novel method and apparatus for both simplifying and improving the introduction of a balloon catheter into a body vessel and for improving the operation thereof.

Still another object of the present invention is to provide an introducer sheath and cooperating adapter for splitting such introducer sheath as it is withdrawn from the body of a patient.

Still another object of the present invention is to provide a novel introducer sheath and cooperating adapter which coacts with the introducer sheath to split the introducer sheath as it is withdrawn from the body of a patient and which provides an excellent blood-tight seal preventing unnecessary loss of blood through the sheath.

Still another object of the present invention is to provide an adapter for use with a thin gauge introducer sheath for use in the percutaneous insertion of an intra-aortic balloon, which adapter includes means for providing a blood-tight seal between the adapter and the balloon catheter extending therethrough and between the adapter and the introducer sheath.

Still another object of the present invention is to provide an adapter with cutters for severing an introducer sheath and a shield for protecting the operator from touching the cutting edges.

The above, as well as other objects of the present invention, will become apparent when reading the accompanying description and drawings in which:

FIG. 4 is a perspective view of an adapter for use with the insertion sheath of FIGS. 3 and 5.

FIGS. 4b-4d show alternative embodiments of the adapter of FIG. 4a.

FIG. 7a is a perspective view of a splittable sheath having a gripping loop.

FIG. 7b is a top plan view of the sheath of FIG. 7a.

FIG. 8a is a plan view of another alternative splittable sheath design.

FIG. 8b is an end view of the sheath of FIG. 8a looking in the direction of arrows 8b-8b.

FIG. 9a is a perspective view of another alternative sheath design.

FIG. 9b is an enlarged end view of the sheath of FIG. 9a.

FIG. 10 is a sectional view of another alternative adapter design.

FIG. 11 is a perspective view of still another alternative adapter design of the present invention.

DETAILED DESCRIPTION OF THE INVENTION

Figure 1:
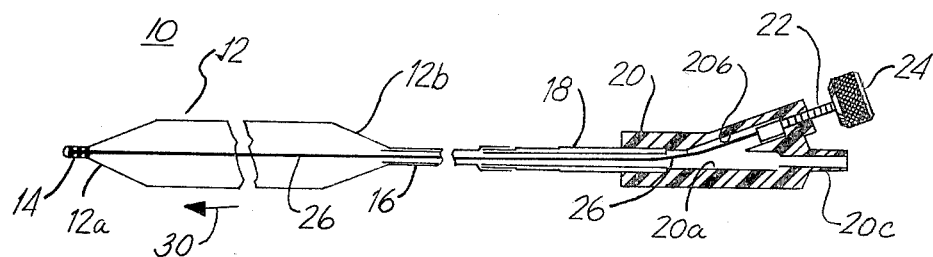
FIG. 1 shows a simplified view of an intra-aortic balloon assembly uniquely adapted for percutaneous insertion.

FIG. 1 shows an intra-aortic balloon assembly 10 especially adapted for percutaneous insertion. The intra-aortic balloon assembly 10 is described in detail in copending application Ser. No. 253,680 filed Apr. 13, 1981. Since a detailed description of the balloon assembly 10 is described in the aforementioned application, a brief description of the balloon assembly will be given herein for purposes of simplicity.

Balloon assembly 10 comprises intra-aortic balloon 12 formed of a thin gauge plastic material which is pliable but which is effectively non-stretchable to substantially precisely limit the maximum diameter of the balloon when fully inflated.

The forward end of the balloon 12 tapers at 12a where it merges with tip 14. The rearward end of balloon 12 tapers at 12b where it merges with balloon catheter 16. Although not shown for purposes of simplicity, the balloon catheter 16 is of a length sufficient to introduce the intra-aortic balloon 12 to a position typically just below the aortic arch, while being assured that the balloon catheter 16 extends well beyond the exterior of the body.

Balloon catheter 16 is joined to coupling 20 by a tubular strain relief member 18. Coupling 20 is provided with a through-bore 20a which terminates at the respective left and right-hand ends of connector 20. A branch bore 20b merges with through-bore 20a and is threaded at its rearward end to threadedly engage tapped member 22 whose right-hand end is secured to knob 24 and whose left-hand end is secured to a thin gauge stylet 26, preferably formed of stainless steel. The left-hand end of stylet 26 is joined to tip 14. The tapered end 20c provided at the right-hand end of coupling 20 is adapted to be joined to a tubular member (not shown for purposes of simplicity) for coupling the intra-aortic balloon assembly 10 to a source capable of providing positive and negative pulsatile pressure to the assembly 10 for repetitively inflating and deflating intra-aortic balloon 12 at a rate to assist the heart in its blood-pumping action. The outer diameter of stylet 26 is quite small so as not to interfere with the pressure pulses introduced into balloon catheter 16.

Figure 2:
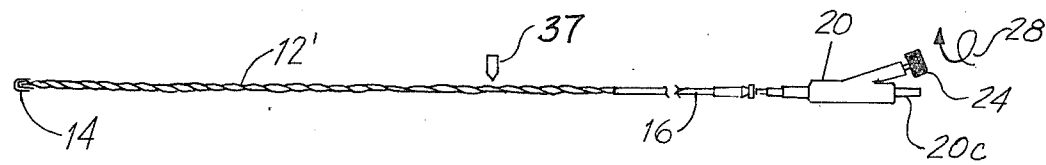
FIG. 2 shows the intra-aortic balloon of FIG. 1 in the twisted configuration in readiness for percutaneous insertion.

In order to prepare intra-aortic balloon assembly 10 for percutaneous insertion, and making reference to both FIGS. 1 and 2, knob 24 is rotated clockwise as shown by arrow 28 in FIG. 2 causing threaded member 22, stylet 26 and tip 14 to rotate in the same direction and to simultaneously move to the left as shown by arrow 30. The rotation of tip 14 is imparted to balloon 12 which is caused to be wrapped up or twisted in the manner shown in FIG. 2, the wrapped-up balloon being represented by numeral 12'. In this wrapped-up condition, the intra-aortic balloon 12' can be seen to present an extremely small profile, i.e. small outer diameter, as compared with its outer diameter as shown in FIG. 1. The lengthening of the intra-aortic balloon 12 assures that the folds formed therein do not double over, thus further guaranteeing a low profile, i.e. small outer diameter, which is especially adapted for percutaneous insertion.

The steps employed in percutaneous insertion are as follows, (noting FIG. 3):

(a) The insertion site 34 is treated with an antiseptic and thereafter a local anesthetic is applied. The femoral artery 36 is located and an angiographic needle (not shown for purposes of simplicity) supplied with the intra-aortic balloon assembly package is inserted into the body and is aligned at a shallow angle relative to the femoral artery 36 (note angle of inserter sheath 40 relative to artery 40) to minimize bending of the balloon catheter 16 as it passes into the body.

(b) A guide wire (not shown) is inserted through the angiographic needle and into the femoral artery to a point beyond the bifurcation.

(c) The intra-aortic balloon is briefly immersed in a saline solution immediately prior to being wrapped up and thereafter is lightly squeezed and twisted between the fingers starting at a location 37 just beyond the right-hand end of intra-aortic balloon 12 (note FIG. 2) and continuing the twisting and stripping operation (in the direction of the wind-up) to the tip 14 in order to force out any air inside of balloon 12 and to help position the layers of the balloon membrane close to one another in an axial direction.

(d) Knob 24 is then rotated through a few turns whereupon the balloon 12 is again stripped in the above manner. These two steps are repeated in an alternating manner until thumbwheel knob 24 has been turned to its stop position and can be turned no further.

(e) The angiographic needle is slipped off of the guide wire and a dilator (not shown) is slipped on to the guide wire and inserted into the body to predilate the insertion path. Thereafter, a large diameter sheath/dilator is then positioned within the artery over the guide wire.

(f) The dilator and guide wire are then removed and the intra-aortic balloon is then introduced into the artery through the sheath 40.

(g) After the intra-aortic balloon 12 is properly positioned, the percutaneous sheath 40, which has originally been introduced into the artery 36 so that its forward end is positioned well into or above the large abdominal aorta, is then withdrawn in an incremental fashion. The portion of the introducer sheath extending outside of the body is pulled apart, also in an incremental fashion, the steps of withdrawal and splitting of the sheath being performed in an alternating fashion.

Figure 3:
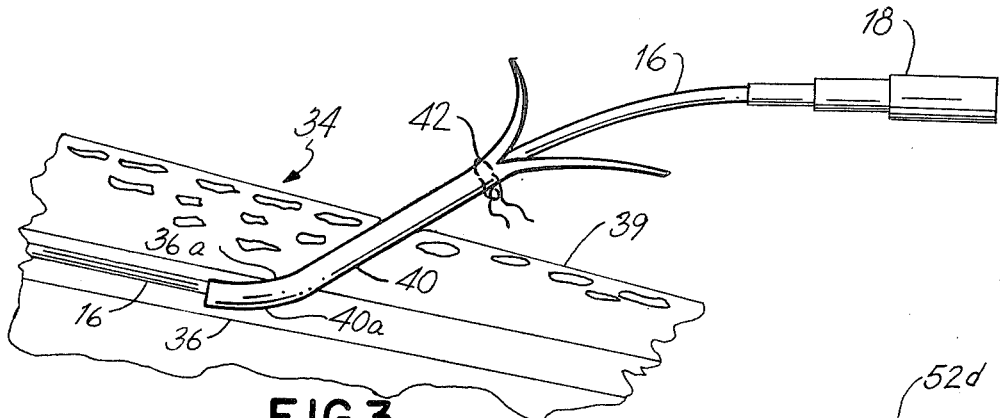
FIG. 3 shows a simplified diagram of a pull-apart insertion sheath especially adapted for percutaneous insertion of an intra-aortic balloon of the type shown in FIGS. 1 and 2.

(h) The introducer sheath 40 shown in FIG. 3 is only partially withdrawn so that its distal end portion 40a partially extends into the femoral artery 36.

(i) The intra-aortic balloon 12 is then unwrapped by rotating thumbwheel 24 counterclockwise. Thereafter the balloon catheter 16 is coupled to the aforementioned pulsatile source (not shown) to initiate augmentation at the correct balloon volume and at the appropriate assist rate. If desired, the position of the balloon 12 may be optimized using fluoroscopy.

In order to reduce bleeding during use, a suture or umbilical cord 42 is placed about sheath 40 at the position shown, for example, in FIG. 3.

For removal, the intra-aortic balloon assembly 10 is disconnected from the pumping system and thumbscrew 24 is turned clockwise to its stop to re-wrap the intra-aortic balloon 12 in the manner shown in FIG. 2 while withdrawing the balloon slightly.

The incremental withdrawal of the balloon 12 from the body and out of the exposed end of sheath 40 (FIG. 3) acts to strip the exposed end of balloon 12 during rewrapping. The balloon 12 is then withdrawn and the opening left in the body of the patient is appropriately treated to prevent a hematoma.

Figures 4, 4B:
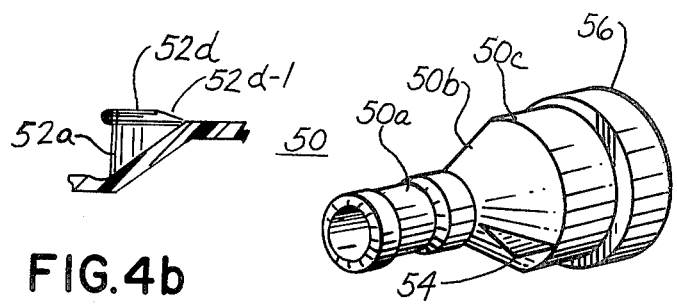
Figure 4C:
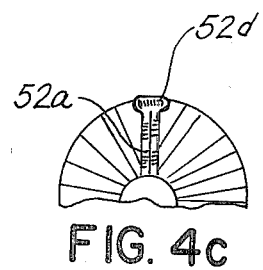
Figure 4D:
Figure 5:
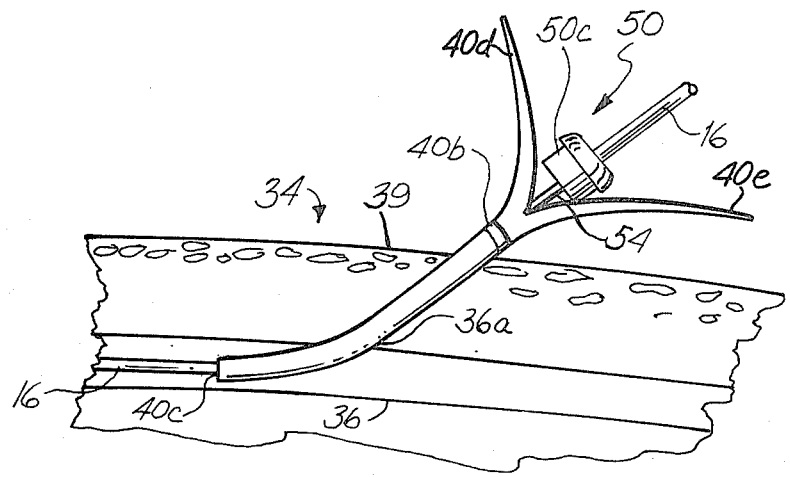
FIG. 5 shows an introducer sheath, balloon catheter and adapter which have been introduced into the body of a patient.
Figure 4A:
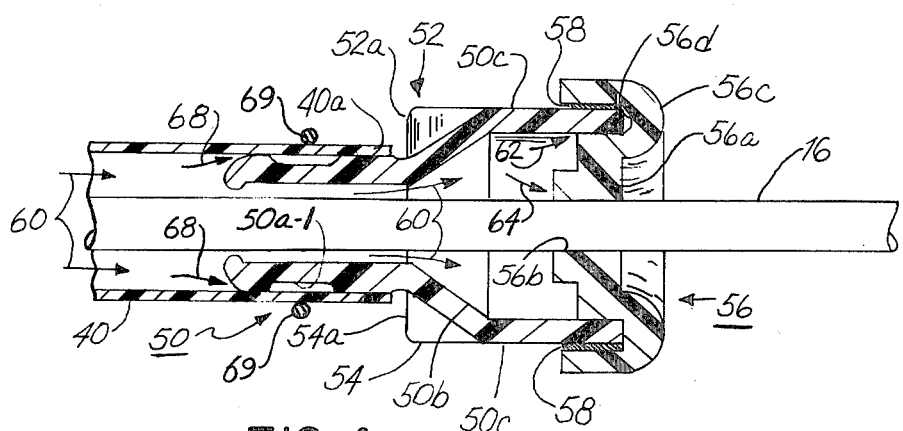
FIG. 4a shows a sectional view of the adapter of FIG. 4 and its coacting arrangement with an introducer sheath and balloon catheter.

In order to facilitate the splitting of the introducer sheath 40 and to provide an extremely effective sliding blood-tight seal, there is provided a balloon catheter adapter 50, shown best in FIGS. 4, 4a and 5. Adapter 50 is a hollow, generally tubular-shaped member having a narrow diameter portion 50a, an intermediate portion 50b whose left-hand end is integral with narrow diameter portion 50a, and tapers outwardly where its right-hand end joins the left-hand end of a larger diameter portion 50c. The hollow interior of adapter 50 permits the free passage of the intra-aortic balloon catheter 16 therethrough.

Adapter 50 is provided with at least one, and preferably a pair, of cutter members 52 and 54 arranged along the outer surface of tapering portion 50b and substantially aligned along a common diameter of adapter 50. Cutter members 52 and 54 are provided with cutting edges 52a and 54a respectively for cutting and splitting introducer sheath 40 in a manner to be more fully described.

The top edge of each cutter member may be enlarged and rounded as shown by portion 52d in FIGS. 4b and 4c to protect the operator from touching the cutting edge 52a. The rearward end 52d-1 of enlarged portion 52d aids in splitting the sheath 40 apart.

As another alternative, the upper portion 52a-1 of cutting edge 52a (see FIG. 4d) may be rounded or smoothed to prevent the operator from engaging the cutting edge 52a.

The right-hand end of larger diameter portion 50c has a seal 56 mounted thereon. Seal 56 is formed of a flexible resilient material, preferably silicone, although any other material having comparable characteristics may be employed. Seal 56 is a substantially circular-shaped member. Central portion 56a thereof is provided with a circular opening 56b for receipt of and sliding engagement with balloon catheter 16. Seal 56 has increased thickness in the immediate region of opening 56a to further enhance the sliding blood-tight seal between seal 56 and balloon catheter 16.

The outer annular portion 56c of seal 56 has a substantially U-shaped configuration as can best be seen from the cross-sectional view of FIG. 4a, to define a continuous annular groove 56d which receives the free end of enlarged diameter portion 50c of adapter 50. A bonding material 58 such as a suitable cement or other similar material which is compatible with the body of the patient so as to prevent the occurrence of any harmful or even annoying reaction, is arranged between adapter 50 and seal 56 to firmly bond seal 56 to adapter 50.

The inner diameter of opening 56b is related to the outer diameter of balloon catheter 16 so that there is at least a slight friction fit therebetween to provide a sliding blood-tight seal which prevents the escape of blood entering into the region between adapter 50 and balloon catheter 16 and represented by arrows 60, whereby any blood moving in the region of the connection between seal 56 and adapter 50, as represented by arrow 62, is prevented and also any blood moving in the region of the sliding seal and represented by arrow 64 is prevented from entering between the seal 56 and balloon catheter 16 so as to exit therethrough.

The manner in which the adapter 50 functions, is as follows:

The end of the balloon catheter 16 remote from the intra-aortic balloon 12 is either inserted through the hollow interior of adapter 50 and through opening 56b of seal 56 or is manufactured to provide the desired sliding arrangement. Thereafter, the free end of catheter 16 is joined to strain relief member 18. It should be understood that balloon catheter 16 is of a length sufficient to position adapter 50 therealong so as not to interfere with the normal operation, including insertion of the intra-aortic balloon assembly 10.

The steps (a) through (f) for percutaneous insertion described hereinabove are repeated. Thereafter, the thin gauge introducer sheath 40 is withdrawn in stages as was described hereinabove and the end 40a of sheath 40 remote from intra-aortic balloon 12 is pushed onto adapter 50 and toward the cutters 52 and 54 causing the free end 40a of introducer sheath 40 to enter upon left-hand end of tapered portion 54b whereupon end 40a undergoes stretching. Thus, the free end 40a is under tension as it engages the cutting edges 52a and 54a, which greatly facilitates the cutting and splitting of sheath 40.

The introducer sheath 40 is split by stages in the manner described hereinabove until, in the preferred embodiment of FIG. 5, the splitting reaches a marker band 40b provided about the outer periphery of introducer sheath 40 for indicating to the operator that the length of the percutaneous sheath between marker band 40b and distal end 40c is just adequate to enable the distal end portion to extend partially into the femoral artery 36 as is shown in FIG. 5.

If desired, the split-apart portion or portions 40d and 40e of the introducer sheath 40 may be cut away so as not to interfere with the handling and/or operation of the intra-aortic balloon assembly 10.

As was described hereinabove, the integrity of the blood-tight seal between adapter 50 and balloon catheter 16 is retained in spite of the sliding movement of adapter 50 along balloon catheter 16. The portion of the introducer sheath 40 which extends over smaller diameter portion 50a of adapter 50 undergoes some stretching and is thereby under tension so as to provide a relatively effective blood-tight seal therebetween so that blood entering into the region between the outer periphery of small diameter portion 50a and introducer sheath 40, as represented by arrow 68, is prevented from exiting therebetween. The adapter 50 which is preferably formed either of a suitable metal such as stainless steel or a suitable plastic, is sufficiently rigid so as to retain its diameter and prevent any reduction in its diameter due to the forces exerted on smaller diameter portion 50a by the stretched introducer sheath 40, so as to prevent any undesirable constriction and/or blockage of balloon catheter 16.

A suture 69 may be placed about the portion of the periphery of sheath 40 surrounding groove 50a-1 in small diameter portion 50a. By tightening the suture 69, the sheath 40 is drawn inwardly and into intimate contact with groove 50a-1 to further enhance the blood-tight seal between sheath 40 and adapter 50. Suture 69 may be knotted to retain sheath 40 in intimate engagement with adapter groove 50a-1.

Figure 6:
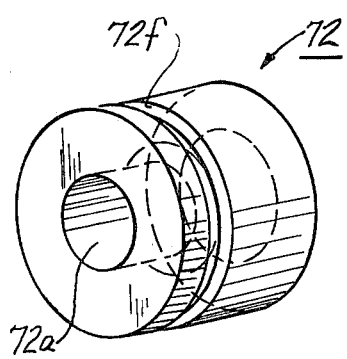
FIG. 6 shows a perspective view of a resilient collar which may be employed with the adapter of the present invention.
Figure 6A:
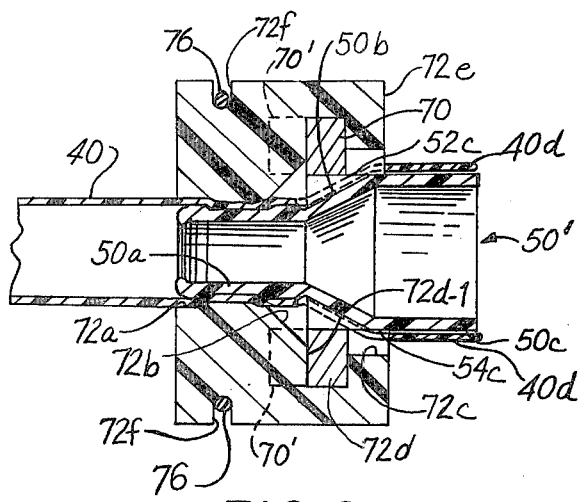
FIG. 6a shows a sectional view of the resilient collar of FIG. 6 and the manner in which it is mounted upon the adapter and sheath to provide a bloodtight seal between the introducer sheath and the adapter.

The blood-tight seal between introducer sheath 40 and adapter 50 may further be enhanced through the alternative embodiment of FIG. 6a wherein the modified adapter identified as 50' in FIG. 6a is substantially identical to the adapter 50 shown in FIGS. 4 and 4a, except for the addition of circular ring 70, which is preferably formed of stainless steel and has portions of its inner diameter joined to edges 52c and 54c of cutting members 52 and 54. FIG. 6a shows a cross-sectional view of circular ring 70 and it can be seen that the cross-section is substantially rectangular in shape.

A resilient, flexible, stretchable collar 72, which is preferably formed of silicone, but which may be formed of any other suitable material, is generally cylindrical in shape and is provided with a through-opening having a narrow diameter portion 72a, a tapering portion 72b, and a larger diameter portion 72c. An internal annular groove 72d is arranged between tapered portion 72b and larger diameter portion 72c and is arranged to receive the outer portion of ring 70. Elastic collar 72 is mounted upon ring 70 by stretching end 72e so that larger diameter portion 72c clears the outer periphery of ring 70. When ring 70 bears against radially aligned sidewall 72d-1 of annular groove 72d, the force applied to stretch end 72e is released causing the elastic collar 72 to contract to its normal configuration and thereby retain itself upon retainer ring 70 in the manner shown in FIG. 6a.

Elastic collar 72 is preferably mounted upon retainer ring 70 after the introducer sheath has been moved over narrow diameter portion 50a of adapter 50. The elastic collar 72, in addition to clinging to ring 70, experiences a finite amount of stretching as a result of the relationship of the inner diameter portion 72a relative to the outer diameter of introducer sheath 40, causing the collar 72 to exert a force upon percutaneous introducer sheath 40 to provide a blood-tight seal between percutaneous sheath 40 and the outer surface of adapter 50. It should be noted that the seal 56 has been omitted from FIG. 6a merely for purposes of simplicity and that the adapter 50' shown in FIG. 6a is also preferably fitted with a seal substantially identical to seal 56 shown in FIGS. 4 and 4a to provide a sliding blood-tight seal between adapter 50' and balloon catheter 16, as was described in detail hereinabove.

The sheath 40 passes between elastic collar 72 and adapter 50. The end of sheath 40 engaging cutting edges 52a, 54a is caused to split apart as the sheath 40 and adapter 50' are moved relative to one another. The split-apart halves of sheath 40 pass on opposite sides of cutting edges 52a, 54a and pass out of the right-hand end of elastic collar 72 as shown by split half 40d in FIG. 6a. Portions of the split halves 40d, 40e (note also FIG. 5) extending beyond the right-hand end of adapter 50' may be cut away.

The blood-tight seal between introducer sheath 40 and adapter 50', shown in FIG. 6a, may be further enhanced by placing a suture 76 within the continuous annular groove 72f provided about the outer periphery of elastic collar 72. The suture 76 is then pulled tight and preferably tied or knotted to further enhance the tightening of sheath 40 about adapter 50'. This procedure may typically be carried out after the introducer sheath has been split apart to the extent desired, thereby avoiding the necessity to continually untie and retie the suture 76. If desired, the suture 76 may be permanently embedded within collar 72 and have its ends exposed for tightening purposes.

Collar 70 also serves to prevent the operator from touching the cutting edges 52a, 54a. If desired, the left-hand end of collar may overlap cutting edges 52a, 54a, as shown in dotted fashion at 70' in FIG. 6a.

FIGS. 7a and 7b show a sheath 80 whose right-hand end is cut or otherwise formed to provide a pair of integral extensions 80a, 80b formed from the bottom half of sheath 80, the top half being cut away and removed. The free ends of extensions 80a, 80b are arranged in overlapping fashion and are joined together by an adhesive cement or other suitable material. Alternatively, a mechanical joining element such as a rivet may be used to join the free ends of extensions 80a, 80b. The joined extensions 80a, 80b form a loop 82 which facilitates gripping by the fingers of an operator to pull the sheath 80 toward the adapter 50, for example, to initiate splitting of the sheath.

FIGS. 8a and 8b show another sheath 84 which may have one end thereof pre-cut to provide a starting slit 86 to facilitate gripping of the sheath 84, as well as facilitating the initiation of the splitting of the sheath. If desired, sheath 84 may be provided with additional slits such as the slit 92 shown in dotted fashion in FIG. 8b. By moving apart the edges of sheath 84 defining slit 86 as shown by arrows 88, 90, one or both of the split halves 84a, 84b may be gripped to move the sheath relative to and against the adapter 50, for example. If desired, one of the halves 84a may have an elongated portion 94 to further simplify gripping. Alternatively, one of the split halves 84b may be cutaway along line 96 and removed, so that the remaining half 84a may be used as a gripping extension.

As was previously mentioned, the peel-apart sheath is expensive and may also peel apart prematurely under certain circumstances. The peel-apart sheath may be substituted by a sheath having greater tear resistance. However, in order to facilitate splitting of the sheath, a design such as is shown in FIGS. 9a and 9b may be employed.

The sheath 96 of FIGS. 9a and 9b may be formed of a suitable plastic meaterial, such as polytetrafluoroethylene. The exterior surface of sheath 96 is scored to provide a score line 98 aligned with the longitudinal axis of sheath 96. The score line extends into the material but not completely through. By drawing sheat 96 over the tapered portion 50b of adapter 50'', see FIG. 11, which adapter is substantially the same as adapter 50 of FIG. 4, except that cutting members 52, 54 have been removed, the sheath 96 is caused to stretch. Due to the significantly reduced thickness of the sheath 96 in the region of the score line 98, the sheath experiences significantly more stretching at this point as compared with the remaining body of the sheath 96. The score line or groove is of sufficient depth to cause the sheath 96 to split along score line 98.

If desired, additional score lines 99–101 may be provided at spaced parallel intervals about the periphery of sheath 96. If desired, the scoring may be arranged on the interior surface of sheath 96 as shown at 102 or may be arranged on both the interior and exterior surfaces as shown by cooperating score line pairs 103a, 103b. The score lines are of a depth sufficient to promote splitting of the sheath when stretched over the tapered portion of an adapter and yet provide sufficient tear strength to prevent splitting during normal use as a percutaneous introducer sheath. If desired, the sheath 96 may also be used in conjunction with the adapter of FIG. 4, having cutting edges 52, 54.

FIG. 10 shows another adapter embodiment 102 of the present invention for use with a peel-apart sheath 116 as was described hereinabove.

The adapter 102 comprises an elongated stainless steel hollow cylindrical member 104 having an outwardly flared end 106 which extends into an internal annular groove 110 provided in an annular-shaped elastic molded silicone member 108. A silicone adhesive 112 is provided upon the exteriior surface of tube 104 and the interior surface of member 108 to secure these members to one another. The diameter of opening 110 at the right-hand end of member 108 is chosen to form a blood-tight sliding seal with the catheter 113 extending therethrough.

A suture 114 may be placed around sheath 116 to enhance the blood-tight seal between sheath 116 and tube 104. The member 108 is provided with a groove 108a for receiving a suture 118 to enhance the blood-tight seal between member 108 and catheter 112. If desired, the adapter 102 may also be used with the scored sheath 96 of FIG. 9a. Annular groove 118 is provided to enable use of adapter 102 with a regular great when employing a surgical technique.

A latitude of modification, change and substitution is intended in the foregoing disclosure and in some instances, some fesatures of the invention may be employed without a corresponding use of other features. Accordingly, it is appropriate that the appended claims be construed broadly and in a manner consistent with the spirit and scope of the invention herein.

As exemplary, less than two cutting edges may be provided upon adapter 50 or, alternatively, more than two cutting edges may be provided, said plural cutting edges being preferably arranged at equally spaced angles about the adapter 50. For exammple, three cutting edges may be provided at 120 degree intervals, four cutting edges may be provided at 90 degree intervals, and so forth.

What is claimed is:

1. Apparatus for percutaneous insertion of an intra-aortic balloon assembly into the body of a patient, said assembly comprising:
   an introducer sheath formed of a material adated to easily split upon the application of a force tending to enlarge the sheath in an outward radial direction, and an intra-aortic balloon assembly including an intra-aortic balloon and cooperating balloon catheter adapted to be inserted into the body of a patient through said introducer sheath;
   adapter means having a central opening arranged for slidably receiving said balloon catheter and including cutting means thereon engageable with said introducer sheath when pressed thereagainst, for cutting and splitting said sheath; and
   said adapter means further including means for providing a blood-tight sliding seal between said adapter means and said balloon catheter.

2. The apparatus of claim 1 further comprising:
   annular mounting means arranged on said adapter means;
   elastic collar means secured to said annular mounting means and having at least a portion thereof encircling the introducer sheath to press the introducer sheath against a portion of the adpater means to provide a blood-tight seal between said introducer sheath and said adapter.

3. The apparatus of claim 1 further comprising:
   means on said adapter means for enlarging the end of the introducer sheath as it is being pressed against said cutting means to place the introducer sheath under tension just prior to being cut so as to facilitate the cutting operation.

4. The apparatus of claim 1 wherein said introducer sheath is provided with an indicia located a predetermined distance inwardly from the distal end of the introducer sheath to facilitate withdrawal of the introducer sheath so that when the aforesaid indicia is exposed beyond the surface of the skin of the patient, this assures that at least a portion of the introducer sheath extends through the perforation in the artery and a predetermined distance along the interior of the artery.

5. The apparatus of claim 1 wherein said introducer sheath is a thin gauge plastic sleeve.

6. The apparatus of claim 5 wherein said plastic is preferably tetrafluoroethylene.

7. The apparatus of claim 1 wherein said introducer sheath is scored.

8. The apparatus of claim 1 wherein said introducer sheath is scored wherein the score line extends over substantially the entire length of said sheath to facilitate splitting of the introducer sheath.

9. The apparatus of claim 8 wherein said score line is substantially parallel to the longitudinal axis of said sheath.

10. The apparatus of claim 9 wherein said sheath is provided with a plurality of spaced parallel score lines.

11. The apparatus of claim 7 wherein the scoring forms a groove in said introducer sheath to sufficiently weaken the sheath in the region of the groove to facilitate splitting of the sheath in the region of the score line when the sheath is stretched and enlarged by said adapter means.

12. The apparatus of claim 1 wherein said sheath is a peel-apart sheath.

13. The apparatus of claim 12 wherein said peel-apart sheath is formed of a grain-oriented plastic material.

14. The apparatus of claim 1 further comprising means on said adapter means for preventing an operator from engaging the cutting means.

15. The apparatus of claim 1 wherein said cutting means comprises a substantially radially aligned cutting edge extending outwardly from said adapter means; and
   means integral with said adapter means and overlying the outer end of said cutting edge for preventing an operator from engaging the cutting edge.

16. The apparatus of claim 15 wherein said means overlying the cutting edge comprises an annular-shaped member overlying the cutting edge.

17. The apparatus of claim 15 wherein the overlying means comprises a radially aligned, smoothed-free surface aligned with and extending beyond said cutting edge.

18. The apparatus of claim 15 wherein said overlying means comprises an enlarged portion integral with and overlying the cutting edge.

19. An intra-aortic balloon assembly designed for percutaneous insertion and including:
   an intra-aortic balloon and cooperating balloon catheter and an introducer sheath for introducing the intra-aortic balloon and balloon catheter into the artery of a patient being treated;
   a cylindrical member having a hollow interior for slidably receiving the balloon catheter therethrough and forming a sliding blood-tight seal with the balloon catheter;
   the exterior surface of said cylindrical member having a small diameter end positioned to engage an adjacent end of the introducer sheath and a large diameter end with a tapering portion intermediate said small and large diameter ends and tapering outwardly from said small diameter end towards said large diameter end; and
   at least one cutting member arranged along said tapered portion for cutting and splitting the introducer sheath as the sheath and cutting member are pressed against one another, said cylindrical member forming a blood-tight seal with said introducer sheath.

20. The adapter means of claim 19 further comprising:
   a resilient seal secured to said adapter means and having an opening for slidably receiving the balloon catheter therethrough and being formed of a resilient compliant material; and
   the opening in said sealing member forming a blood-tight sliding seal with said balloon catheter.

21. The apparatus of claim 19 wherein said cutting member has a cutting edge positioned inwardly from the tapered surface of said cylindrical member whereby the introducer sheath is caused to be stretched and placed under tension as it is drawn over said tapered portion and before it reaches said cutting edge to facilitate the cutting and slitting operation.

22. The apparatus of claim 20 wherein said compliant sealing member is joined to the large diameter end of said adapter means.

23. The apparatus of claim 19 further comprising an annular mounting ring joined to said adapter means; and
   an elastic collar joined to said mounting ring and overlying said small diameter portion for tightening a portion of the introducer sheath overlying said small diameter portion and beneath said elastic collar to provide a blood-tight seal between the introducer sheath and the adapter means.

24. The apparatus of claim 19 further comprising an annular ring surrounding said adapter means and overlying the cutting edge to protect an operator from engaging the cutting edge.

25. The apparatus of claim 19 further comprising an enlarged portion integral with and overlying the cutting member to protect an operator from engaging the cutting edge.

26. Adapter means for use with a peel-apart introducer sheath and a balloon catheter, said adapter means comprising:
a hollow, elongated rigid tube having an outwardly flared end;
an annular shaped resilient compliant member having one end thereof mounted upon the flared end of said tube and having an internal annular slot for receiving the flared end of said tube;
means for securing the engaging surfaces of said tube and said compliant member;
said compliant member having an axial bore extending therethrough in communication with the hollow tube to permit the passage of a catheter therethrough;
the end portion of said bore remote from the flared end of said tube having an inner diameter cooperating with the outer surface of said catheter to cooperatively from a sliding blood-tight seal therebetween; and
the outer diameter of said tube remote from said flared end having a diameter which cooperates with the inner surface of said sheath to form a sliding blood-tight seal therebetween.

27. The adapter means of claim 26 wherein the outer periphery of said compliant member is provided with an annular groove spaced from and arranged to surround said end portion providing the blood-tight sliding seal for receiving a suture which may be tightened about said compliant member to enhance the last-mentioned blood-tight sliding seal.

28. The apparatus of claim 5 wherein said sheath is provided with a pair of integral extensions, the free ends of said extensions being joined to form a loop to facilitate gripping by an operator.

29. The apparatus of claim 5 wherein said sheath is provided with a pre-cut slit extending inwardly a predetermined distance from one end of said sheath to facilitate gripping and/or splitting.

30. The apparatus of claim 5 wherein one end of said sheath is provided with at least one integral extension to facilitate gripping of said sheath.

* * * * *